(12) United States Patent
Gabrielii et al.

(10) Patent No.: US 8,652,113 B2
(45) Date of Patent: *Feb. 18, 2014

(54) DISPOSABLE ABSORBENT ARTICLE COMPRISING A PRINTED TAG

(75) Inventors: Inge Gabrielii, Västra Frölunda (SE); Ulrika Carlson, Billdal (SE); Hans Een, Mölnlycke (SE); Maria Bogren, Askim (SE); Sofia Hermansson, Västra Frölunda (SE)

(73) Assignee: SCA Hygiene Products AB, Gothenburg (SE)

( * ) Notice: Subject to any disclaimer, the term of this patent is extended or adjusted under 35 U.S.C. 154(b) by 10 days.

This patent is subject to a terminal disclaimer.

(21) Appl. No.: 13/126,991

(22) PCT Filed: Oct. 30, 2008

(86) PCT No.: PCT/SE2008/000617
§ 371 (c)(1),
(2), (4) Date: Sep. 12, 2011

(87) PCT Pub. No.: WO2010/050853
PCT Pub. Date: May 6, 2010

(65) Prior Publication Data
US 2011/0313388 A1  Dec. 22, 2011

(51) Int. Cl.
*A61F 13/15* (2006.01)
(52) U.S. Cl.
USPC .............. 604/385.01; 604/396; 604/385.13
(58) Field of Classification Search
USPC ............................... 604/385.01, 396, 385.13
See application file for complete search history.

(56) References Cited

U.S. PATENT DOCUMENTS

| | | | |
|---|---|---|---|
| 3,704,710 A * | 12/1972 | Fifer | 604/398 |
| 5,226,992 A | 7/1993 | Morman | |
| 6,352,526 B1 | 3/2002 | Weber et al. | |
| 6,476,289 B1 | 11/2002 | Buell et al. | |
| 6,558,499 B1 | 5/2003 | Pargass et al. | |
| 2006/0058745 A1 | 3/2006 | Pires | |
| 2007/0250023 A1 | 10/2007 | Strannemalm | |

(Continued)

FOREIGN PATENT DOCUMENTS

| CN | 1753628 A | 3/2006 |
|---|---|---|
| CN | 102202620 A | 9/2011 |

(Continued)

*Primary Examiner* — Jacqueline F. Stephens
(74) *Attorney, Agent, or Firm* — Drinker Biddle & Reath LLP

(57) ABSTRACT

A disposable absorbent article intended to be worn around the waist of a wearer includes a chassis having a front portion, a back portion, and a crotch portion there between, and optionally a waistband. A printed tag is arranged on the inner wearer facing side of the chassis in at least one of the front portion, back portion, and the waistband. The tag has at least one first area which is fixedly attached to the chassis and at least one second area which is unattached. The first fixedly attached area covers an area of at least 5% of the total area of the tag and the second unattached area has a length extending along a side edge of the tag of at least 5 mm and a width of at least 1 mm. The tag as described makes it easier to differentiate between the front and back of the article.

22 Claims, 7 Drawing Sheets

(56) References Cited

U.S. PATENT DOCUMENTS

| | | |
|---|---|---|
| 2007/0265591 A1 | 11/2007 | Loritz et al. |
| 2008/0051744 A1 | 2/2008 | Cummings |
| 2008/0132872 A1 | 6/2008 | Trennepohl et al. |
| 2008/0221543 A1 | 9/2008 | Wilkes et al. |
| 2009/0209174 A1* | 8/2009 | Gonzales ................... 450/57 |

FOREIGN PATENT DOCUMENTS

| | | |
|---|---|---|
| EP | 0 646 062 | 8/1996 |
| EP | 1 035 818 | 4/2002 |
| JP | 10-43235 | 2/1998 |
| JP | 2003/153940 | 5/2003 |
| JP | 2005/137582 | 6/2005 |
| JP | 2005/237768 | 9/2005 |
| WO | 98/29251 | 7/1998 |
| WO | 03/000165 | 1/2003 |
| WO | 2004/075801 | 9/2004 |
| WO | 2005/122984 | 12/2005 |
| WO | WO-2008/107804 | 9/2008 |

* cited by examiner

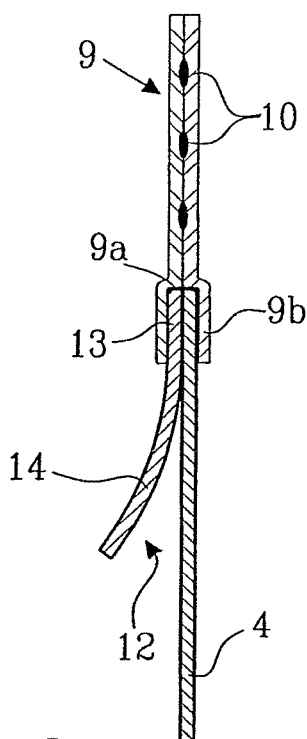
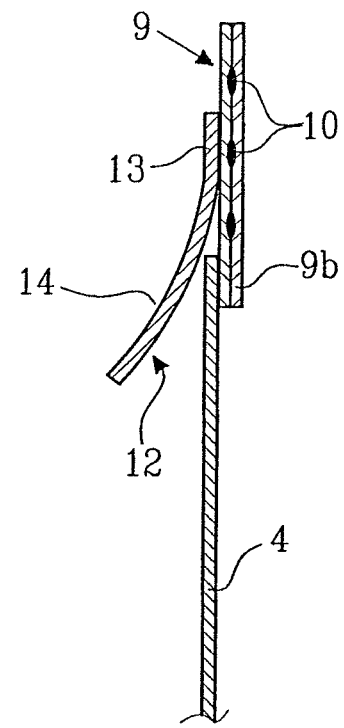
Fig.3
Fig.4A
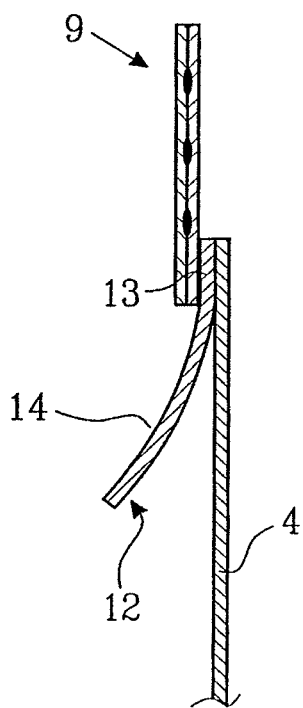
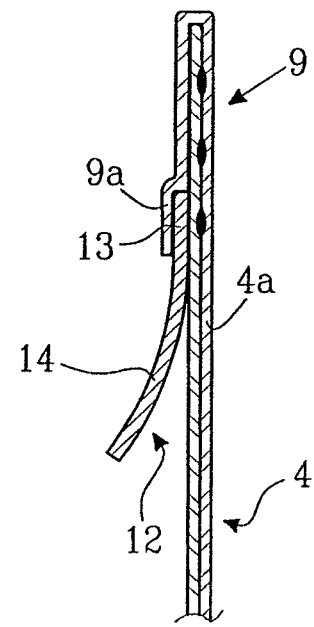
Fig.4B
Fig.4C

DISPOSABLE ABSORBENT ARTICLE COMPRISING A PRINTED TAG

CROSS-REFERENCE TO PRIOR APPLICATION

This application is a §371 National Stage Application of PCT International Application No. PCT/SE2008/000617 filed Oct. 30, 2008.

FIELD OF THE INVENTION

The present disclosure refers to a disposable absorbent article such as a diaper, pant diaper, a sanitary pant or incontinence garment, intended to be worn around the waist of a wearer. The article includes a printed tag.

BACKGROUND

Absorbent articles having a chassis are supposed to be worn like a pair of pants and to have a comfortable fit about the wearer. The article includes a front region and a back region that either may be fastened together by means of fasteners like adhesive tapes of mechanical fasteners, for example hook and loop fasteners, to assume a pant-like shape. Alternatively, the front and back portions are interconnected along the longitudinal sides to form a pant-like absorbent article. In a further alternative, the article is provided with belt members, usually at the back region, which are intended to be fastened together around the waist of the wearer, and subsequently the front region is fastened to the belt members.

For pant articles, like pant diapers, sanitary pants and incontinence pants, it is also desirable that the articles are capable of being pulled up and down over the hips of the wearer to allow the wearer or caregiver to easily put on and remove the article when it has been soiled. Such absorbent pants can be made with elasticized stretchable side panels and waist portion, usually including elastic members, such as elastic threads, contractibly affixed between the backsheet and the topsheet.

Further, at least portions of the chassis of absorbent articles can be made of an elastic material, such as elastic laminates. Such laminates may include an elastic layer, for example an elastic film or nonwoven, which has been stretched and sandwiched between outer layers of fibrous layers. An elastic laminate may also be formed of a plurality of elastic threads which are attached in a stretched conditions between layers of material, for example nonwoven materials.

Examples of absorbent articles which in part are made of elastic laminates are for example found in U.S. Pat. No. 6,476,289, JP 10043235 and WO2005/122984.

Disposable absorbent articles are intended for single use and are not adapted to be laundered and reused, as regular underwear. Many absorbent articles, especially pant articles, are similar in appearance, size and shape as regular underwear and there is a trend towards making disposable absorbent articles more and more underwear-like. For example adult users of disposable incontinence garments want these to be as discrete and underwear-like as possible.

Many caregivers as well as users of absorbent articles have a problem differentiating between the front and back of an absorbent article. Normally it is important for a proper fit and absorption characteristics to wear the article in a correct way. Many elderly adults have poor eye sight which can add to the problem of identifying the front and back of the absorbent article, for example an incontinence pant, and thus properly positioning the article on the body.

US 2007/0265591 discloses a disposable absorbent article including a removable indicium on the waistband for facilitating the identification of the back or front of the article and to thereby promote a correct fitting of the article to the body. The indicium may be in the form of a printed label which is removably attached to the waistband or a label printed with a heat activated ink that will become less visible when maintained at a temperature for a predetermined period of time. The idea is that the user of the article does not want the brand name to remain or appear on the article during or after use. There is however a risk that the label will come loose unintentionally before use of the article or during use, in case it is not removed before use.

There is therefore still room for improvement with respect to making the absorbent article more underwear-like and making it easier to identify the back or front of an absorbent garment intended to be worn around the waist of a wearer.

SUMMARY

It is desired to provide an absorbent article such as a diaper, pant diaper, a sanitary pant or incontinence garment, intended to be worn around the waist of a wearer, where the article includes a chassis having a front portion, a back portion, and a crotch portion there between. Optionally, the article includes a waistband. The article further includes an absorbent core secured to the chassis in at least the crotch portion. The article has features which makes it easier to differentiate between the front and the back of the article even for persons with poor eye sight and in bad light conditions.

In a first aspect, an article includes a printed tag arranged on the inner wearer facing side of the chassis in one of the front and back portions, the printed tag having at least one first area which is fixedly attached to the chassis and at least one second area which is unattached. The first fixedly attached area covers an area of at least 5% of the total area of the tag and the second unattached area has a length, l, extending along a side edge of the tag of at least 5 mm and a width, w, of at least 1 mm.

The term "fixedly attached" refers to the tag being attached to the chassis so that it is not intended to be separated or disconnected during normal use of the absorbent article.

In one embodiment, the first fixedly attached area covers an area of at least 10%, preferably at least 15%, of the total area of the tag.

In a further embodiment, the second unattached area has a length, l, extending along a side edge of the tag of at least 7 mm, preferably at least 10 mm.

In a still further embodiment, the second unattached area has a width, w, of at least 3 mm.

In one aspect of the invention, the second unattached area of the tag is located between two opposite side edges of the tag, the opposite side edges being fixedly attached to the chassis.

In a further aspect of the invention, the tag is attached to the chassis by an adhesive, by thermal or ultrasonic bonding or combinations thereof.

In a still further aspect, the chassis includes an elastic waistband, wherein part of the tag or the entire tag is attached to the waistband.

In one embodiment, the elastic waistband includes at least one ply of web material that is joined with an overlap to at least one of the front and back portions of the chassis, and that at least a part of the first fixedly attached area of the tag is located on, in or under the waistband and that the second unattached area of the tag extends below the waistband.

In a further embodiment, the absorbent article is a pant article including an elastic waistband, wherein the front and back portions of the chassis are joined together along their longitudinal sides.

In one aspect of the invention, the tag material of the unattached area has a Bending rigidity according to Kawabata of not more than 0.1 gf·cm$^2$/cm, preferably not more than 0.05 gf·cm$^2$/cm.

In a further aspect, the tag has at least one of Surface roughness and Friction according to Kawabata which differs at least 10% from the Surface roughness or Friction respectively according to Kawabata of the surrounding area of the chassis to which the tag is attached. In particular embodiments, the tag has at least 10% higher Surface roughness or Friction according to Kawabata than the surrounding area of the chassis to which the tag is attached. In a further aspect, the tag has at least one of Surface roughness and Friction according to Kawabata which differs at least 20%, preferably at least 30% from the Surface roughness or Friction according to Kawabata of the surrounding area of the chassis to which the tag is attached.

In one embodiment, the tag is attached to an elastic material, such as an elastic waistband or an elastic laminate constituting at least a part of the chassis.

In a still further aspect, the tag has been attached to the elastic material with the elastic material held in a stretched condition so that the tag is wrinkled when the elastic material is in a relaxed condition, wherein the wrinkled tag will exhibit a higher Surface roughness or Friction according to Kawabata than the surrounding elastic material of the chassis.

BRIEF DESCRIPTION OF THE DRAWINGS

FIG. 3 is a cross section according to the line III-III in FIG. 2F.

FIG. 4 A-C are cross sections similar to FIG. 3 but illustrating different embodiments of a waistband.

DETAILED DESCRIPTION OF PREFERRED EMBODIMENTS

Figure 1:
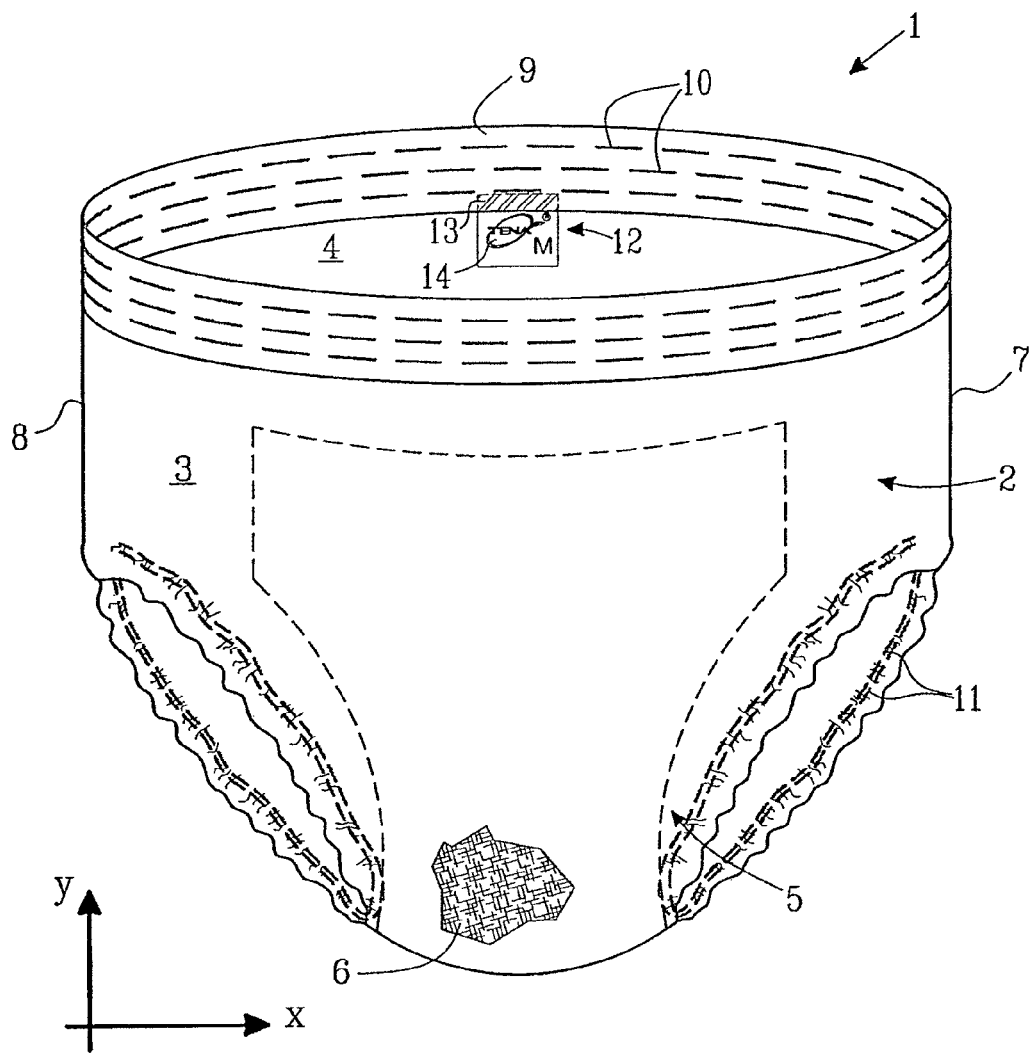
FIG. 1 shows a perspective view of a pant diaper.

FIG. 1 of the drawings shows an embodiment of a pant-type absorbent article 1 for an infant or an incontinent adult. The pant article includes a chassis 2 having a front portion 3, a back portion 4 and a crotch portion 5 there between. The article further includes an absorbent core 6 secured to the chassis in at least the crotch portion. The crotch portion 5 is herewith defined as the narrow part of the article intended to be worn in the wearer's crotch between the legs. Usually the absorbent core 6 extends into the front and back portions of the article.

The article has a transverse direction, x, and a longitudinal direction, y.

The front and back portions 3 and 4 are joined together by a pair of side seams 7 and 8 to form a unitary article having a waist opening and a pair of leg openings. The side seams can be formed in a variety of ways known in the art, such as ultrasonic welding, adhesive or a combination thereof. One or both side seams may further be openable and refastenable, wherein they are formed by mechanical fasteners or adhesive tape. In a further embodiment the front and back portions may be joined via a pair of elastic side panels.

In an alternative embodiment, the absorbent article is a so called open diaper, which has no side seams between the front and back portions 3 and 4. Fastening means in the form of mechanical fasteners or adhesive tape are provided at the side edges of the back portions and are intended to be fastened to the external surface of the front portion.

In a still further embodiment, the absorbent article is a so called belted diaper or incontinence garment including a pair of opposed laterally extending belt members usually attached to the back portion at the waist portion thereof. These belt portions are adapted to be wrapped around the waist of the wearer of the garment and fastened together by means of first fastening means, such as an adhesive tape or mechanical fastening means, for example a hook-and-loop fastener. The front portion is then passed between the legs of the wearer and fastened to the outside of the belt members by means of second fastening means provided at the waist portion of the front portion.

The absorbent core 6 is normally enclosed between a liquid permeable topsheet and a liquid impermeable backsheet. The topsheet can include a nonwoven material, e g spunbond, meltblown, carded, hydroentangled, wetlaid etc. Suitable nonwoven materials can be composed of natural fibers, such as woodpulp or cotton fibers, manmade fibers, such as polyester, polyethylene, polypropylene, viscose etc. or from a mixture of natural and manmade fibers. The topsheet material may further be composed of tow fibers, which may be bonded to each other in a bonding pattern, as e.g. disclosed in EP-A-1 035 818. Further examples of topsheet materials are porous foams, apertured plastic films etc. The materials suited as topsheet materials should be soft and non-irritating to the skin and intended to be readily penetrated by body fluid, e.g. urine or menstrual fluid. The topsheet may be different in different parts of the absorbent article.

The liquid impervious backsheet covering the absorbent core on the garment-facing side thereof is of a liquid impervious material, such as a thin plastic film, e.g. a polyethylene or polypropylene film, a nonwoven material coated with a liquid impervious material, a hydrophobic nonwoven material, which resists liquid penetration or a laminate including plastic films and nonwoven materials. The backsheet material may be breathable so as to allow vapour to escape from the absorbent core, while still preventing liquids from passing therethrough. Examples of breathable backsheet materials are microporous polymeric films, nonwoven laminates from spunbond and meltblown layers, laminates from microporous polymeric films and nonwoven materials. In particular embodiments, the backsheet is inelastic in the crotch area. The backsheet in parts of the areas of the absorbent core extending into the front and/or back region may however, if desired, be elasticized by means of elastic members, such as elastic threads contractibly affixed between layers of the backsheet material or between the absorbent core and the backsheet.

The absorbent core 6 can be of any conventional kind. Examples of commonly occurring absorbent materials are cellulosic fluff pulp, tissue layers, highly absorbent polymers (so called superabsorbents), absorbent foam materials, absorbent nonwoven materials or the like. It is common to combine cellulosic fluff pulp with superabsorbents in an absorbent body. It is also common to have absorbent bodies including layers of different material with different properties with respect to liquid receiving capacity, liquid distribution capacity and storage capacity. The thin absorbent bodies, which are common in for example baby diapers and incontinence guards, often include a compressed mixed or layered structure of cellulosic fluff pulp and superabsorbent. The size and absorbent capacity of the absorbent core may be varied to be suited for different uses such as for infants or for incontinent adults.

The areas of the chassis 2 outside of the absorbent core 6 may be formed of the topsheet and the backsheet joined together to form a laminate structure. Alternatively at least part of the chassis outside the absorbent core area is made of another web material, which provides comfort and breathability. One example of a pant absorbent article of this type is shown in WO2005/122984, in which a part of the chassis covering the front and back portions 3 and 4 comprises an elastic web material in the form of an elastic laminate. Such an elastic web materials may be composed in a number of different ways.

One example is an elastic laminate including first and second outer layers of fibrous material and a middle elastic film layer. Other types of elastic web materials are elastic nonwoven materials, nonwoven materials which per se are inelastic, but which have been elastified by means of elastic members, such as elastic threads, contractibly affixed between the nonwoven layers. The elastic web materials may include one layer or two or more layers that have been laminated.

Examples of elastic laminates are described in EP-B-0 646 062, WO 98/29251, WO 03/000165 and U.S. Pat. No. 5,226, 992. Examples of commercially available elastic laminates are FlexAire™ from Tredegar and PK 6358 from Nordenia.

In particular embodiments, the elastic web material have an elasticity of at least 30%, preferably at least 50%, more preferably at least 70%, at least in the transverse direction, x, of the article as measured in the elasticity test as described below.

A major part of the front and back portions 3 and 4 may alternatively be made of an inelastic material and elasticized side panels may be provided in the sides of the pant article in the area bridging the front and back portions.

The absorbent article shown in FIG. 1 further includes an elastic waistband 9, which forms a part of the chassis 2. The elastic waistband 9 may include a separate band of nonwoven layers having a plurality of elastic members, such as elastic threads 10, contractibly affixed there between. The waistband is fixed by ultrasonic welding, thermal bonding or by an adhesive to the upper edge of the front and back portions 3 and 4. The waistband may be attached to the inner body facing surface of the front and back portions (FIG. 4B) or the outer garment facing surface thereof (FIG. 4A). Alternatively one ply 9a of the waistband is attached to the inner surface and one ply 9b to the outer surface of the back and front portions respectively (FIG. 3).

In an alternative embodiment, there is no separate waistband and elastification of the waist area may be provided by elastic threads contractibly affixed close to the upper edge of the front and back regions. One such embodiment is disclosed in FIG. 4C, in which a waistband is formed by elastic threads contractibly affixed between two plies 4a and 4b of a laminate structure forming at least part of the back portion 4 and/or front portion, and wherein one ply 4a is longer than the other ply and folded over and attached to the inside of the respective back region/front region of the chassis. The folded over ply 4a provides a soft waist edge, but may in an alternative embodiment be eliminated.

Open diapers and belted diapers usually do not have any elastic waistband. An elastic portion, a so called waist elastics, may be incorporated in part of the back and/or front portion adjacent the waist opening area.

The leg openings of the absorbent article may be elasticized, said elastification is usually accomplished by a plurality of elastic members 11, such as elastic threads, which are contractibly affixed to the chassis. The article may also be provided by so called barrier cuffs, in order to provide an improved security against leakage. These barrier cuffs may in some instance replace leg elastics.

The absorbent article includes a tag 12 printed with symbols such as brand name, logotype, size indication, the wording "back" or "front", back/front indication, absorption level, artwork etc. The tag 12 is fixedly attached on the inner wearer facing side of the chassis, preferably to the back portion 4 and/or to the waistband 9 attached to the back portion. The tag provides a visual indicator for differentiating between the front and back portion of the article and thereby facilitate proper fitting of the article to the wearer. Alternatively, the tag can be attached to the front portion 3 and/or to the waistband 9 attached to the front portion to aid a young child to properly step into the article. Young children tend to look at the front of a pant article and align it with the stomach rather than searching for a back indicator. Adults, however, are often used to labels in ordinary underwear that are located at the back of the underwear. An adult would therefore likely associate a tag or label with the back portion of a pant. Since ordinary underwear usually is provided with a tag having printed thereon brand name, logotype, size, washing instructions etc. the provision of such a tag will make the absorbent article more underwear-like and enhance the appearance of the absorbent article.

The tag 12 is shown to have a rectangular shape, but may of course have any optional shape. The size can vary but, in particular embodiments, it has a dimension in the transverse direction, x, of the article of at least 10 mm and up to 80 mm and in longitudinal direction, y, of at least 10 mm and up to 90 mm.

The tag 12 has at least one first area 13 which is fixedly attached to the chassis and at least one second area 14 which is unattached. The term "fixedly attached" refers to the tag being attached to the chassis so that it is not intended to be separated or disconnected during normal use of the absorbent article. The first fixedly attached area 13 and the second unattached area may be configured in many different ways and some examples are shown in FIG. 2 A-G. Thus, the unattached area 14 may extend along a side edge of the tag 12 as shown in FIG. 2-A, C, and D or be located between two opposite side edges of the tag 12, the opposite side edges being fixedly attached to the chassis, as is shown in FIG. 2B, or combinations thereof as shown in FIG. 2D. The unattached area 14 should not be entirely surrounded by fixedly attached areas 14, but must extend to at least one side edge of the tag 12 in order to be easily felt by the fingertips.

Figure 2A:
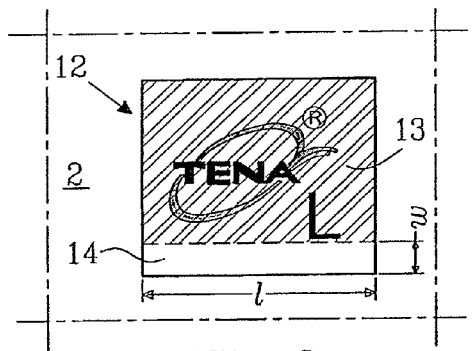
FIG. 2 A-G show simplified plan views of a printed tag attached to the chassis of an absorbent article.
Figure 2B:
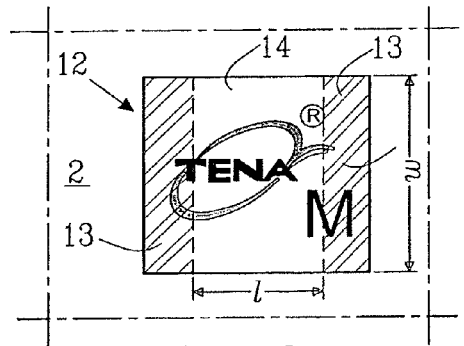
Figure 2C:
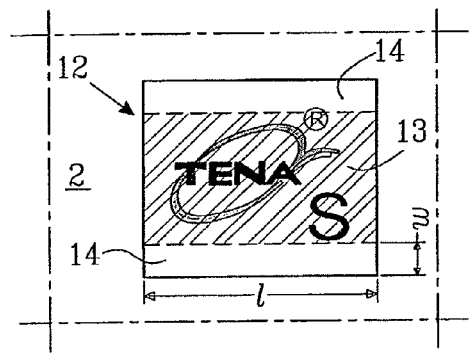
Figure 2D:
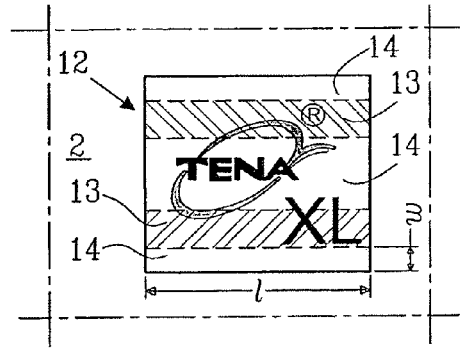
Figure 2E:
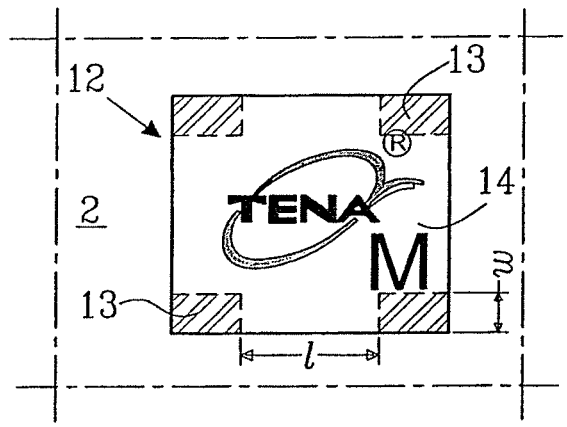
Figure 2F:
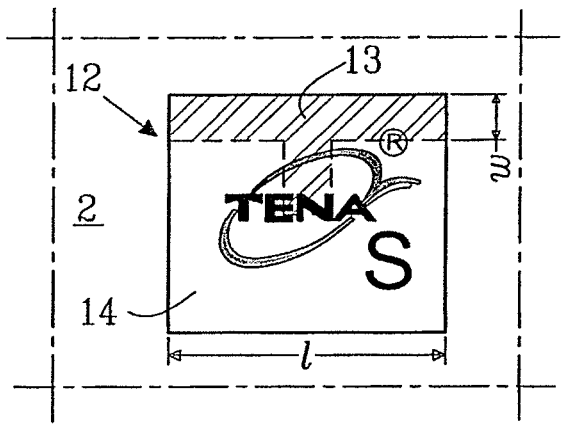

In the embodiment of FIG. 2E the fixedly attached areas 13 are arranged in the corners of the tag. The fixedly attached areas do not need to be applied in all corners of the tag, but for example only in two corners. FIG. 2F illustrates a T-shaped attachment area.

Figure 2G:
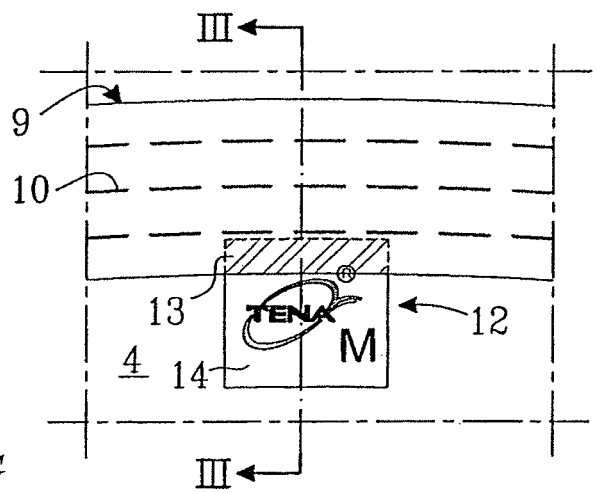

In the embodiment shown in FIG. 2G, a part of the tag is applied to an elastic waistband 9. It may either be attached on the waistband as illustrated in FIG. 4A, under the waistband as illustrated in FIG. 4B, or in the waistband 9 as illustrated in FIGS. 3 and 4C. The fixedly attached area 14 may be the area located under the interior ply 9a or 4a respectively of the waistband and the unattached area 14 is the area extending outside the waistband. Part of the area extending outside the waistband may of course be fixedly attached to the chassis as well.

The first fixedly attached area 13 should be large enough to provide a secure attachment of the tag 12 and should therefore have a dimension adapted to the size of the tag. In order to fulfil a secure attachment the first fixedly attached area 13 should amount to at least 5% of the surface area of the tag, preferably at least 10%, and more preferably at least 15%. The attached area 13 should, in particular embodiments, be sufficiently large to allow the print on the tag to be readily visible.

The second unattached area 14 should be large enough to be possible to feel by the fingertips and should therefore extend along a side edge of the tag along a length, l, of at least 5 mm, preferably at least 7 mm, and more preferably at least 10 mm, and have a width, w, transverse to the side edge of at least 1 mm, preferably at least 3 mm.

In the embodiments shown in FIGS. 2A, 2C, and 2D, the unattached area 13 extends along the entire length of a side edge of the tag 12 having a rectangular shape. In FIG. 2B, an embodiment is shown in which the unattached area 13 is located between two opposite side edges of the tag 12, the opposite side edges being fixedly attached to the chassis 2. In this embodiment, the unattached area 13 may have a length, l, along a side edge, of at least 7 mm, preferably at least 10 mm in order to be easily perceptible by a fingertip.

The unattached area 14 has the function of making it easier for a person with poor eye sight and to make it possible under bad light conditions to identify the tag 12 with the fingertips and thereby differentiate between the front and back of the article.

A central unattached area 14 as shown in FIG. 2B may further be used to hang the article on a hook for example.

In particular embodiments, the tag 12 is made of a nonwoven material suited for printing on. Examples of suitable materials are spunbond, meltblown and laminates thereof, for example SMS materials (spunbond-meltblown-spunbond), embossed plastic film, laminates of plastic/film/nonwoven, textile material etc.

In order for the tag not to give skin irritations or be noticeable when the product is worn by a wearer, the bending rigidity of the unattached portion 14 of the tag is a parameter of interest. Usual laundry tags in normal underwear are commonly accepted. The tag material should, in particular embodiments, have a Bending rigidity according to Kawabata of not more than 0.1 gf·cm$^2$/cm, preferably not more than 0.05 gf·cm$^2$/cm, in order to ensure that the unattached portion 14 will not cause any skin irritation. This value is calculated as a mean value of the bending rigidity in MD and CD directions.

The attachment of the tag 12 to the chassis 2 is made by adhesive, ultrasonic welding or thermal bonding preferably by adhesive. In embodiments where the tag is applied under the waistband 9 as shown in for example FIG. 2F and FIG. 3 it may be attached by thermal bonding or ultrasonic welding, when thermal bonding or ultrasonic welding is used for attaching the waistband to the front/back portion. Combinations of adhesive and thermal bonding or ultrasonic welding may be used as well.

In order to provide a fixed attachment of the tag 12 that also withstands shear forces during use of the article, the shear force of the attachment should be sufficiently high as well as the peel force.

In the process for attaching the tag to the article, the attachment, for example adhesive, does not have to be applied all the way to at least one side edge of the tag, which simplifies the process and reduces the risk that adhesive ends up outside the tag area, where it may cause skin irritations.

In order to enhance the possibility to differentiate the tag 12 from the surrounding portions of the chassis 2 by the fingertips, the tag 12 may have a surface structure that differs from the surrounding parts of the chassis. One way of measuring surface structure of web material is by the Surface roughness according to the Kawabata test described below.

According to one embodiment, the Surface roughness and/or Friction according to Kawabata of the tag differ at least 10%, preferably at least 20% and more preferably at least 30% from the Surface roughness and/or Friction respectively of the surrounding area of the chassis to which the tag is attached. The percentage is calculated based on the value of the surrounding area of the chassis outside the tag. In particular embodiments, the Surface roughness and/or Friction of the tag is/are higher than that of the surrounding chassis.

Figure 5:
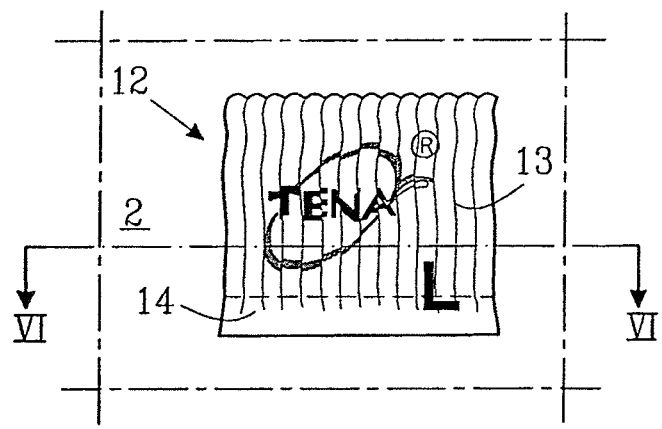
FIG. 5 is a simplified plan view of a further embodiment of a printed tag attached to the chassis of an absorbent article.
Figure 6:
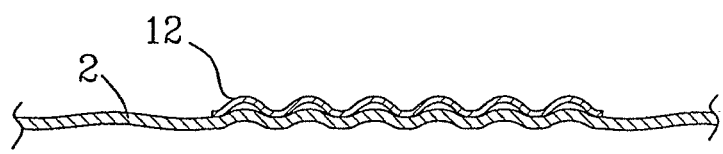
FIG. 6 is a cross section according to the line V-V in FIG. 5.
Figure 7:
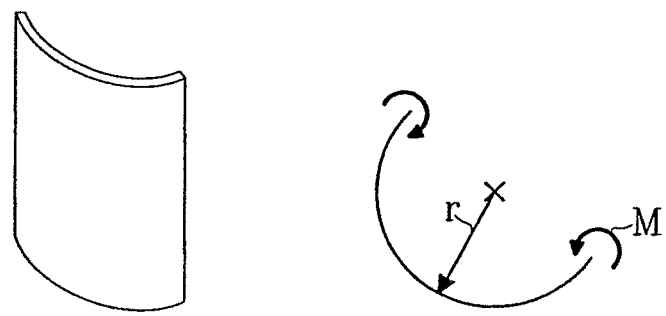
FIG. 7 illustrates the method for measuring Bending rigidity according to Kawabata.

One way of accomplishing the higher Surface roughness and Friction is when attaching the tag to an elastic material, wherein the elastic material is held in a stretched condition while attaching the tag, so that when the elastic material is relaxed the tag will wrinkle. This is illustrated in FIGS. 5 and 6 of the drawings. The elastic material should be stretched at least 30%, preferably at least 50%, over its length in relaxed condition during the attachment of the tag. The wrinkled tag will exhibit a higher Surface roughness and Friction according to Kawabata than the surrounding elastic material of the chassis in a relaxed state of the elastic material. This will make it easier to differentiate the tag from the surrounding elastic material by the fingertips. However, when the elastic material is in a stretched condition, such as when it is worn on the body of a user, the wrinkled tag will smooth down, and the Surface roughness and Friction decrease. This reduces a possible risk for skin irritations caused by the tag.

Elasticity Test

The method measures how an elastic material behaves at repeated load and unload cycles. The sample is stretched to a predetermined elongation and a cyclic movement between 0 and the predetermined elongation is performed. Desired load and unload forces are recorded. The permanent, i.e. remaining, elongation of the relaxed material is measured.

A tensile tester, Lloyd LRX, able to perform cyclic movements and equipped with a printer/plotter or software presentation is used. The sample is prepared by cutting it to a width of 25 mm and a length that is preferably 20 mm longer than the distance between the clamps in the tensile tester.

The tensile tester is calibrated according to the apparatus instructions. The parameters needed for the test (load and unload forces) are adjusted to:

Crosshead speed: 500 mm/min
Clamp distance: 50 mm
Preload: 0.05 N

The sample is placed in the clamps according to the marks and it is made sure that the sample is centered and fastened perpendicularly in the clamps. The tensile tester is started and three cycles between 0 and the predetermined elongation, equal to the highest defined 1$^{st}$ load, are performed. Before the last cycle, the sample is relaxed for 1 minute, then the permanent elongation is measured by stretching the sample until a force of 0.1 N is detected and the elongation is read.

The permanent elongation after relaxation should be less than 10% and is measured by the method above. Thus an elasticity of 30% is defined as that the laminate should have a permanent relaxation after elongation of less than 10% after being exerted to an elongation of 30% in the tensile tester above. An elongation of 30% means an elongation to a length that is 30% longer than the initial length of the sample.

Kawabata Tests

The Kawabata KES-FB is a Japanese quality judgment system used for textile materials and is disclosed in: *The Standardization and Analysis of Hand Evaluation* (2nd Edition), Sueo Kawabata, July 1980, The Hand Evaluation and Standardization Committee, The Textile Machinery Society of Japan.

Special recommendations for nonwoven materials are set up in: *A Proposal of the Standardized Measuring Conditions for Mechanical Property of Apparel Fabric*, by Kawabata S och Niwa M. These recommendations have been followed in the tests below.

The Kawabata test is divided into four blocks: KES-FB-1 for tensile- and shear measurements, KES-FB-2 for pure bending measurements, KES-FB-3 for compression measurements and KES-FB-4 for surface measurements. Examples of output data obtained from Kawabata tests are:
Extensibility (%)
Bending rigidity (gf·cm$^2$/cm)
Shear stiffness (gf/cm·degree)
Compressibility (%)
Surface roughness (μm)
Friction (–)

The unit gf used in the Kawabata system is the force which gravity exerts on one gram, i.e. about 9.81 mN. In the below tests, Bending rigidity (KES-FB-2), Surface roughness and Friction (KES-FB-4) modules have been used. A general description of these tests is given below.

Bending Rigidity

The Bending rigidity is measured by clamping the sample between two clamps at a distance of 10 mm and bending the sample to a bending radius of r=+4 mm, wherein the force is registered. The method prescribes a clamping width of 20-200 mm depending on sample. The force is plotted against l/r, wherein r is the bending radius. The Bending rigidity is calculated from the inclination of the graph between l/r=0.5 cm$^{-1}$ and l/r=1.5 cm$^{-1}$ and is the mean value of the Bending Rigidity in MD and CD.

Friction

Figure 8A:
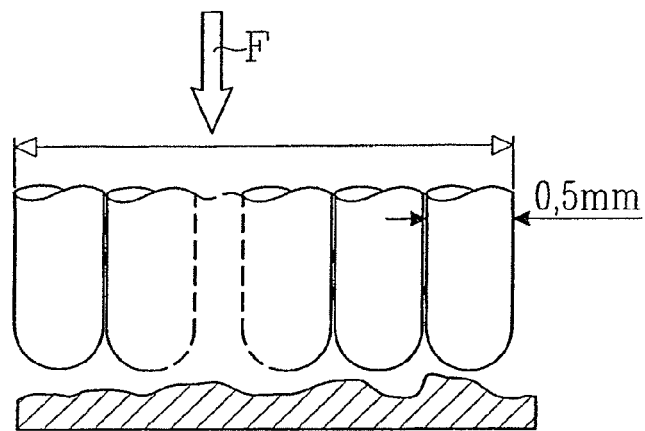
FIGS. 8 A and B illustrates the method for measuring Friction according to Kawabata.
Figure 8B:
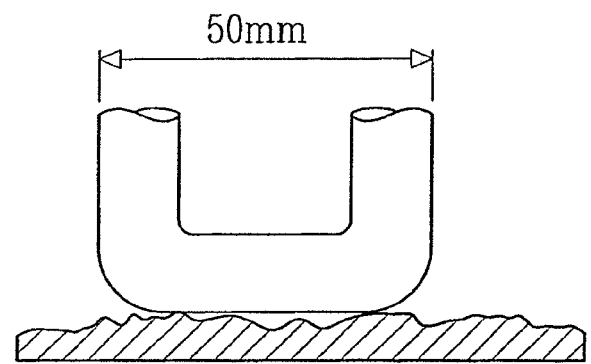

The Friction according to Kawabata is measured by drawing a "sledge" according to FIGS. 8A and 8B 20 mm along the sample surface at which the force is measured. The speed in this measurement is 1 mm/s and the normal force F is kept constant at 50 gf.

Surface Roughness

Figure 9A:
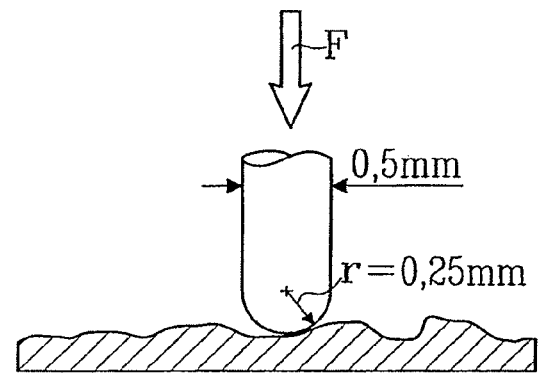
FIGS. 9 A and B illustrates the method for measuring Surface roughness according to Kawabata.
Figure 9B:
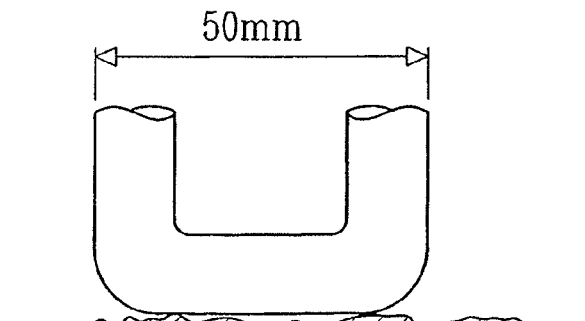

The bulb for the Surface roughness measurements include a smooth metal thread having a shape according to FIGS. 9A and 9B. It is loaded with a constant force of 10 gf and moves with a speed of 1 mm/s in 20 mm back and forth once over the sample surface. In the direction of movement, the samples were fixed with a force of 140 g/200 mm. The Surface roughness is defined as the mean deviation from the thickness of the sample measured in the unit μm.

EXAMPLES

Kawabata measurements have been made on samples with respect to Bending Rigidity, Friction and Surface Roughness:
Bending Rigidity A sample material in the form of a SMMS (spunbond-meltblown-meltblown-spunbond) laminate from Fibertex A/S, Denmark, basis weight 23 gsm, suited as a tag material, was tested with respect to Bending rigidity according to Kawabata. As a reference sample a textile tag material used in ordinary underwear as a laundry tag was also tested with respect to Bending rigidity according to Kawabata.

The Bending Rigidity was measured both in MD and CD and a mean value between MD and CD was calculated. The size of the samples was adjusted between 20 and 200 mm in order to give bending forces within measurable range. In the table below, the values are recalculated to be comparable regardless of sample size. The results are presented in Table 1 below and are mean values of three measurements.

TABLE 1

| | Bending rigidity MD (gf · cm$^2$/cm) | Bending rigidity CD (gf · cm$^2$/cm) | Mean (gf · cm$^2$/cm) |
|---|---|---|---|
| Sample | 0.045 | 0.017 | 0.031 |
| Reference sample | 0.186 | 0.042 | 0.114 |

Friction and Surface Roughness

Kawabata measurements have been made on samples of an elastic laminate (elastic film/nonwoven) FlexAire™ from Tredegar having attached thereon a tag of a SMS (spunbond-meltblown-spunbond) laminate, basis weight 20 gsm. The tag was adhesively attached to the elastic laminate with a glue amount of 15 gsm. The size of the tag was 60×50 mm. The tag was attached to the elastic laminate with this held in a stretched condition, so that the tag was wrinkled upon relaxation of the laminate. The measurements were performed in the relaxed state. When the product is fully stretched out, the tag width is 60 mm and the material was measured at a relaxed state. In this state, the width of the tag is only 37.8 mm, i.e. 63% of fully stretched width.

Figure 10:
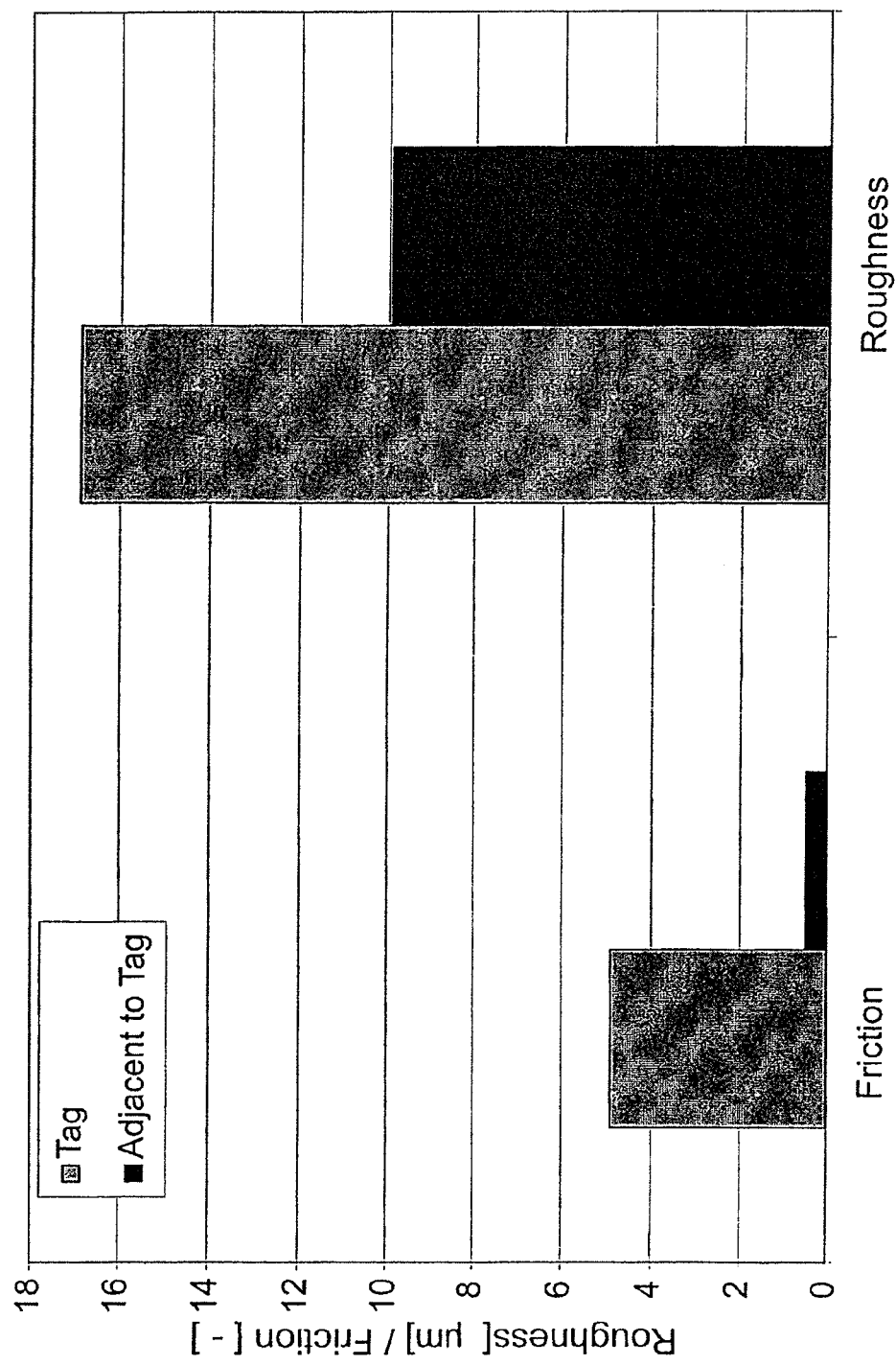
FIG. 10 are staple diagrams illustrating the results from Friction and Surface roughness measurements.

Surface roughness and Friction were measured on the tag material (attached to the elastic laminate) as well as on the elastic laminate adjacent the tag. The measurements were made in only one direction (across the wrinkles) with the elastic laminate in a relaxed condition. The Surface roughness as well as the Friction of the wrinkled tag was higher than for the adjacent laminate elastic laminate and this difference was clearly possible to sense with the fingertips. The results are shown in the staple diagram of FIG. 10.

When stretching the elastic laminate the wrinkles of the tag will smooth down and the difference in Surface roughness and Friction with respect to the adjacent elastic laminate will decrease, thus making the tag less possible to sense when worn on the body. This is beneficial for the wearer comfort since a low Surface roughness and Friction is known to cause less chafe.

The invention claimed is:

1. A disposable absorbent article intended to be worn around the waist of a wearer, said article comprising:
   a chassis having a front portion, a back portion and a crotch portion there between, and optionally comprises a waistband; and
   an absorbent core secured to the chassis in at least the crotch portion,
   wherein a printed tag is arranged on the inner wearer facing side of the chassis in at least one of said front portion, back portion, and said waistband, said article having a longitudinal (y) and a transverse (x) direction,
   wherein said printed tag has at least one first area which is fixedly attached to the chassis and at least one second area which is unattached, the unattached area of the tag has a Bending rigidity according to Kawabata of not more than 0.1 gf·cm$^2$/cm, and wherein the first fixedly attached area covers an area of at least 5% of the total area of the tag and the second unattached area has a length extending along a side edge of the tag of at least 5 mm and a width of at least 1 mm.

2. The absorbent article as claimed in claim 1,
wherein said second unattached area of the tag is located between two opposite side edges of the tag, said opposite side edges being fixedly attached to the chassis.

3. The absorbent article as claimed in claim 1,
wherein the tag is attached to the chassis by an adhesive, by thermal or ultrasonic bonding or combinations thereof.

4. The absorbent article as claimed in claim 1,
wherein the chassis comprises an elastic waistband and wherein part of the tag or the entire tag is attached to the waistband.

5. The absorbent article as claimed in claim 4,
wherein said elastic waistband comprises at least one ply of web material that is joined with an overlap to at least one of said front and back portions of the chassis, wherein at least a part of said first fixedly attached area of the tag is located on, in or under the waistband and wherein said second unattached area of the tag extends below the waistband.

6. The absorbent article as claimed in claim 1,
wherein said article is a pant article comprising an elastic waistband and wherein the front and back portions of the chassis are joined together along their longitudinal sides.

7. The absorbent article as claimed in claim 1, wherein material of the unattached area of the tag has a Bending rigidity according to Kawabata of not more than 0.05 gf·cm$^2$/cm.

8. A disposable absorbent article intended to be worn around the waist of a wearer, said article comprising:
a chassis having a front portion, a back portion and a crotch portion there between, and optionally comprises a waistband; and
an absorbent core secured to the chassis in at least the crotch portion,
wherein a printed tag is arranged on the inner wearer facing side of the chassis in at least one of said front portion, back portion, and said waistband, said article having a longitudinal (y) and a transverse (x) direction,
wherein said printed tag has at least one first area which is fixedly attached to the chassis and at least one second area which is unattached,
wherein the first fixedly attached area covers an area of at least 5% of the total area of the tag and the second unattached area has a length extending along a side edge of the tag of at least 5 mm and a width of at least 1 mm, and
wherein the tag has at least one of a Surface roughness and a Friction according to Kawabata which differs at least 10% from the Surface roughness or Friction according to Kawabata of the surrounding area of the chassis to which the tag is attached.

9. The absorbent article as claimed in claim 8,
wherein the tag has a higher Surface roughness or Friction according to Kawabata than the surrounding area of the chassis to which the tag is attached.

10. The absorbent article as claimed in claim 8,
wherein the tag has at least one of a Surface roughness and a Friction according to Kawabata which differs at least 20% from the Surface roughness or Friction according to Kawabata of the surrounding area of the chassis to which the tag is attached.

11. The absorbent article as claimed in claim 10, wherein the tag has at least one of a Surface roughness and a Friction according to Kawabata which differs at least 30% from the Surface roughness or Friction according to Kawabata of the surrounding area of the chassis to which the tag is attached.

12. The absorbent article as claimed in claim 8,
wherein said second unattached area of the tag is located between two opposite side edges of the tag, said opposite side edges being fixedly attached to the chassis.

13. The absorbent article as claimed in claim 8,
wherein the tag is attached to the chassis by an adhesive, by thermal or ultrasonic bonding or combinations thereof.

14. The absorbent article as claimed in claim 8,
wherein the chassis comprises an elastic waistband and wherein part of the tag or the entire tag is attached to the waistband.

15. The absorbent article as claimed in claim 14,
wherein said elastic waistband comprises at least one ply of web material that is joined with an overlap to at least one of said front and back portions of the chassis, wherein at least a part of said first fixedly attached area of the tag is located on, in or under the waistband and wherein said second unattached area of the tag extends below the waistband.

16. The absorbent article as claimed in claim 8,
wherein said article is a pant article comprising an elastic waistband and wherein the front and back portions of the chassis are joined together along their longitudinal sides.

17. A disposable absorbent article intended to be worn around the waist of a wearer, said article comprising:
a chassis having a front portion, a back portion and a crotch portion there between, and optionally comprises a waistband; and
an absorbent core secured to the chassis in at least the crotch portion,
wherein a printed tag is arranged on the inner wearer facing side of the chassis in at least one of said front portion, back portion, and said waistband, said article having a longitudinal (y) and a transverse (x) direction,
wherein said printed tag has at least one first area which is fixedly attached to the chassis and at least one second area which is unattached,
wherein the first fixedly attached area covers an area of at least 5% of the total area of the tag and the second unattached area has a length extending along a side edge of the tag of at least 5 mm and a width of at least 1 mm, and
wherein the tag has been attached to an elastic material with the elastic material held in a stretched condition so that the tag is wrinkled when the elastic material is in a relaxed condition, and wherein the wrinkled tag will exhibit a higher Surface roughness or Friction according to Kawabata than the surrounding elastic material of the chassis.

18. The absorbent article as claimed in claim 17,
wherein said second unattached area of the tag is located between two opposite side edges of the tag, said opposite side edges being fixedly attached to the chassis.

19. The absorbent article as claimed in claim 17,
wherein the tag is attached to the chassis by an adhesive, by thermal or ultrasonic bonding or combinations thereof.

20. The absorbent article as claimed in claim 17,
wherein the chassis comprises an elastic waistband and wherein part of the tag or the entire tag is attached to the waistband.

21. The absorbent article as claimed in claim 20,
wherein said elastic waistband comprises at least one ply of web material that is joined with an overlap to at least one of said front and back portions of the chassis, wherein at least a part of said first fixedly attached area of the tag is located on, in or under the waistband and wherein said second unattached area of the tag extends below the waistband.

22. The absorbent article as claimed in claim 17,
wherein said article is a pant article comprising an elastic waistband and wherein the front and back portions of the chassis are joined together along their longitudinal sides.

\* \* \* \* \*